(12) United States Patent
Esken et al.

(10) Patent No.: US 9,163,024 B2
(45) Date of Patent: Oct. 20, 2015

(54) TRIS SALTS OF 8-CHLORO-3-PENTYL-3,7-DIHYDRO-1H-PURINE-2,6-DIONE

(75) Inventors: Holly Esken, Durham, NC (US); Beth Adams Norton, Durham, NC (US)

(73) Assignee: GlaxoSmithKline LLC, Wilmington, DE (US)

( * ) Notice: Subject to any disclaimer, the term of this patent is extended or adjusted under 35 U.S.C. 154(b) by 751 days.

(21) Appl. No.: 13/133,486

(22) PCT Filed: Dec. 7, 2009

(86) PCT No.: PCT/US2009/066941
§ 371 (c)(1),
(2), (4) Date: Jun. 8, 2011

(87) PCT Pub. No.: WO2010/068581
PCT Pub. Date: Jun. 17, 2010

(65) Prior Publication Data
US 2011/0251218 A1   Oct. 13, 2011

Related U.S. Application Data

(60) Provisional application No. 61/120,596, filed on Dec. 8, 2008.

(51) Int. Cl.
*A61K 31/522* (2006.01)
*C07D 473/06* (2006.01)
*C07D 473/04* (2006.01)

(52) U.S. Cl.
CPC ............ *C07D 473/06* (2013.01); *C07D 473/04* (2013.01)

(58) Field of Classification Search
CPC .............................. C07D 473/06; C07D 473/04
USPC ...................................... 544/271; 514/263.34
See application file for complete search history.

(56) References Cited

U.S. PATENT DOCUMENTS

| | | | |
|---|---|---|---|
| 3,657,327 A | 4/1972 | Morozowich | |
| 4,647,585 A | 3/1987 | Loots et al. | |
| 7,713,982 B2 | 5/2010 | Pinto | |
| 8,143,264 B2 | 3/2012 | Hatley et al. | |
| 8,268,839 B2 | 9/2012 | Pinto et al. | |
| 8,394,808 B2 | 3/2013 | Pinto et al. | |
| 2003/0013905 A1 | 1/2003 | Huang | |
| 2007/0135456 A1 | 6/2007 | Pinto et al. | |
| 2009/0209561 A1 | 8/2009 | Hatley et al. | |
| 2010/0010021 A1 | 1/2010 | Pinto et al. | |
| 2010/0160354 A1 | 6/2010 | Pinto et al. | |
| 2010/0168122 A1 | 7/2010 | Hatley et al. | |
| 2013/0150383 A1 | 6/2013 | Pinto et al. | |

FOREIGN PATENT DOCUMENTS

WO    WO 2005/077950 A3    8/2005
WO    WO 2005077950 A2 *   8/2005    ........... C07D 473/00

OTHER PUBLICATIONS

Gu, Leo. Pharmaceutical research, vol. 4, No. 3, 1987.*
Ortego, Monica. Atherosclerosis 147 (1999) 253-261.*
Ganji, Shobha. Journal of Nutritional Biochemistry 14 (2003) 298-305.*
Berge, et al. Journal of Pharmaceutical Sciences, 66:1-19 (1977).
M. R. Caira. Topics in Current Chemistry, 198: 163-208 (1998).

* cited by examiner

*Primary Examiner* — Golam M M Shameem
*Assistant Examiner* — Laura Daniel
(74) *Attorney, Agent, or Firm* — Linda E. Hall; John E. Lemanowicz (57) ABSTRACT

The present invention relates to a tris salt of 8-chloro-3-pentyl-3,7-dihydro-1H-purine-2,6-dione of Formula (A) or a pharmaceutically acceptable salt thereof:

Formula (A)

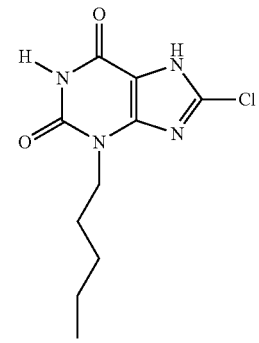

corresponding pharmaceutical formulations, manufacture processes and uses of the aforementioned compound in therapy, particularly in treatment of diseases where under-activation of the HM74A receptor contributes to the disease or where activation of the receptor will be beneficial.

11 Claims, 6 Drawing Sheets

TRIS SALTS OF 8-CHLORO-3-PENTYL-3,7-DIHYDRO-1H-PURINE-2,6-DIONE

This application is a 371 of International Application No. PCT/US2009/066941, filed 07 Dec. 2009, which is incorporated herein by reference. This application claims priority to and the benefit of U.S. Provisional Application No. 61/120,596.

TECHNICAL FIELD OF THE INVENTION

The present invention relates to a particular novel salt of 8-chloro-3-pentyl-3,7-dihydro-1H-purine-2,6-dione.

In particular, the present invention relates to a trishydroxymethylaminomethane (tris) salt of 8-chloro-3-pentyl-3,7-dihydro-1H-purine-2,6-dione (i.e., also defined as 8-chloro-3-pentyl-3,7-dihydro-1H-purine-2,6-dione trishydroxymethylaminomethane (i.e. CAS), or 8-chloro-3-pentyl-3,7-dihydro-1H-purine-2,6-dione 2-amino-2-(hydroxymethyl)-1,3-propanediol (i.e. IUPAC)), herein referred to as the compound of Formula (IA), pharmaceutical formulations comprising said compound, processes for its preparation and uses thereof.

BACKGROUND OF THE INVENTION

PCT International Patent Publication WO2005/077950 (SmithKline Beecham Corporation) discloses therapeutically active xanthine compounds of Formula (I):

Formula (I)

corresponding manufacture processes of said compounds, pharmaceutical formulations containing said active compounds and the use of the compounds in therapy, particularly in the treatment of diseases where under-activation of the HM74A receptor contributes to the disease or where activation of the receptor will be beneficial.

The compound 8-chloro-3-pentyl-3,7-dihydro-1H-purine-2,6-dione (i.e. the free acid form) is described in Example 12 as Formula (A) in PCT International Patent Application Publication No. WO2005/077950:

Formula (A)

WO2005/077950 is incorporated by reference in its entirety.

The present invention now identifies a novel tris salt of 8-chloro-3-pentyl-3,7-dihydro-1H-purine-2,6-dione ("Formula (A)" as identified above), also known as 8-chloro-3-pentyl-3,7-dihydro-1H-purine-2,6-dione trishydroxymethylaminomethane (i.e. CAS) or 8-chloro-8-chloro-3-pentyl-3,7-dihydro-1H-purine-2,6-dione-2-amino-2-(hydroxymethyl)-1,3-propanediol (i.e., IUPAC)) (i.e., where the term tris is an abbreviation of the organic compound known as trishydroxymethylaminomethane, with the formula $(HOCH_2)_3CNH_2$). The tris salt of 8-chloro-3-pentyl-3,7-dihydro-1H-purine-2,6-dione (Formula (A)) is herein referred to as Formula (IA), Formula (IA)

The tris salt (Formula (IA)) is superior to the free acid (Formula (A)) as defined above. In particular, the tris salt has been shown to exhibit enhanced physical stability particularly when compared to the free acid form. By the term "enhanced physical stability" it is meant that the tris salt will remain in its original form and will not readily convert (or partially convert) to another form by hydration during essential manufacturing processes. In contrast, the free acid has been found to readily convert to a hydrated form during aqueous based processing steps, for example during wet granulation.

Additionally, the tris salt has a higher solubility than the free acid, with an increased $C_{max}$ and decreased $T_{max}$, which indicates faster absorption.

SUMMARY OF THE INVENTION

In one aspect, the invention relates to a tris salt of 8-chloro-3-pentyl-3,7-dihydro-1H-purine-2,6-dione, i.e., also known as 8-chloro-3-pentyl-3,7-dihydro-1H-purine-2,6-dione trishydroxymethylaminomethane (i.e. CAS) or 8-chloro-3-pentyl-3,7-dihydro-1H-purine-2,6-dione-2-amino-2-(hydroxymethyl)-1,3-propanediol (i.e., IUPAC) (Formula (IA)).

In another aspect, the compound of Formula (IA) is an anhydrate. In this context, the word anhydrate means the absence of water in the crystal lattice.

The compound of Formula (IA) may be amorphous or crystalline. In one aspect, the compound of Formula (IA) is crystalline.

In one aspect, the compound of Formula (IA) as an anhydrate in crystalline form is characterised by an x-ray powder diffraction (XRPD) pattern comprising the following peaks:

| Position (±0.2° 2-theta) | d-spacing (Å) |
|---|---|
| 10.1 | 8.7 |
| 10.5 | 8.4 |
| 12.2 | 7.3 |

-continued

| Position (±0.2° 2-theta) | d-spacing (Å) |
|---|---|
| 13.0 | 6.8 |
| 13.5 | 6.5 |
| 17.3 | 5.1 |

In another aspect, the compound of Formula (IA) as an anhydrate in crystalline form is characterised by an XRPD pattern comprising the following peaks:

| Position (±0.2° 2-theta) | d-spacing (Å) |
|---|---|
| 10.1 | 8.7 |
| 10.5 | 8.4 |
| 12.2 | 7.3 |
| 13.0 | 6.8 |
| 13.5 | 6.5 |
| 17.3 | 5.1 |
| 17.5 | 5.1 |
| 17.9 | 5.0 |
| 18.3 | 4.8 |
| 19.2 | 4.6 |
| 19.8 | 4.5 |
| 20.2 | 4.4 |
| 20.6 | 4.3 |
| 20.9 | 4.2 |
| 21.7 | 4.1 |
| 22.1 | 4.0 |
| 23.3 | 3.8 |
| 23.9 | 3.7 |
| 24.6 | 3.6 |
| 26.3 | 3.4 |
| 27.1 | 3.3 |
| 27.9 | 3.2 |
| 28.2 | 3.2 |
| 28.6 | 3.1 |
| 29.6 | 3.0 |

Figure 1:
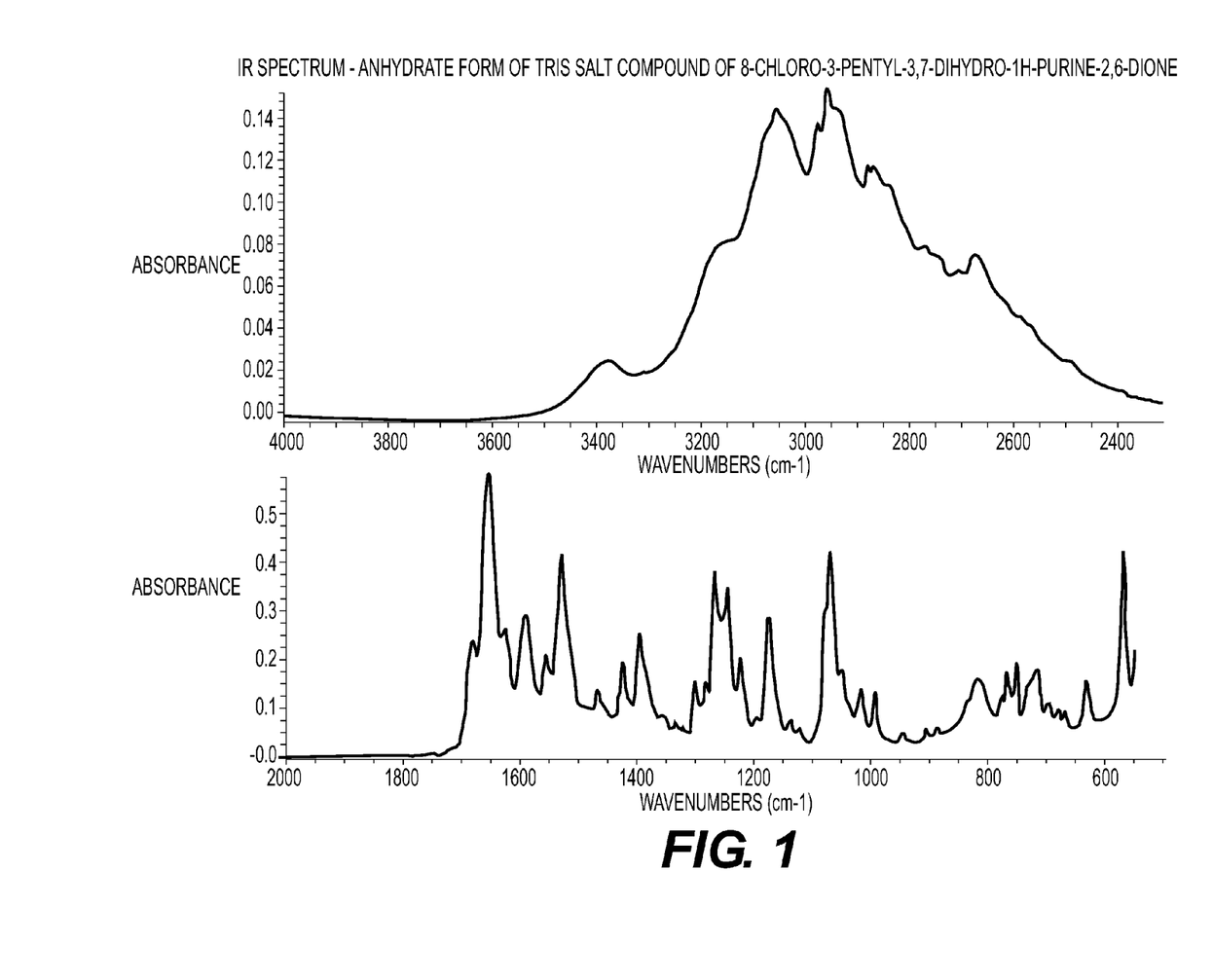
FIG. 1 shows an IR Spectrum of the anhydrate form of the tris salt of 8-chloro-3-pentyl-3,7-dihydro-1H-purine-2,6-dione (Formula (IA)).
Figure 2:
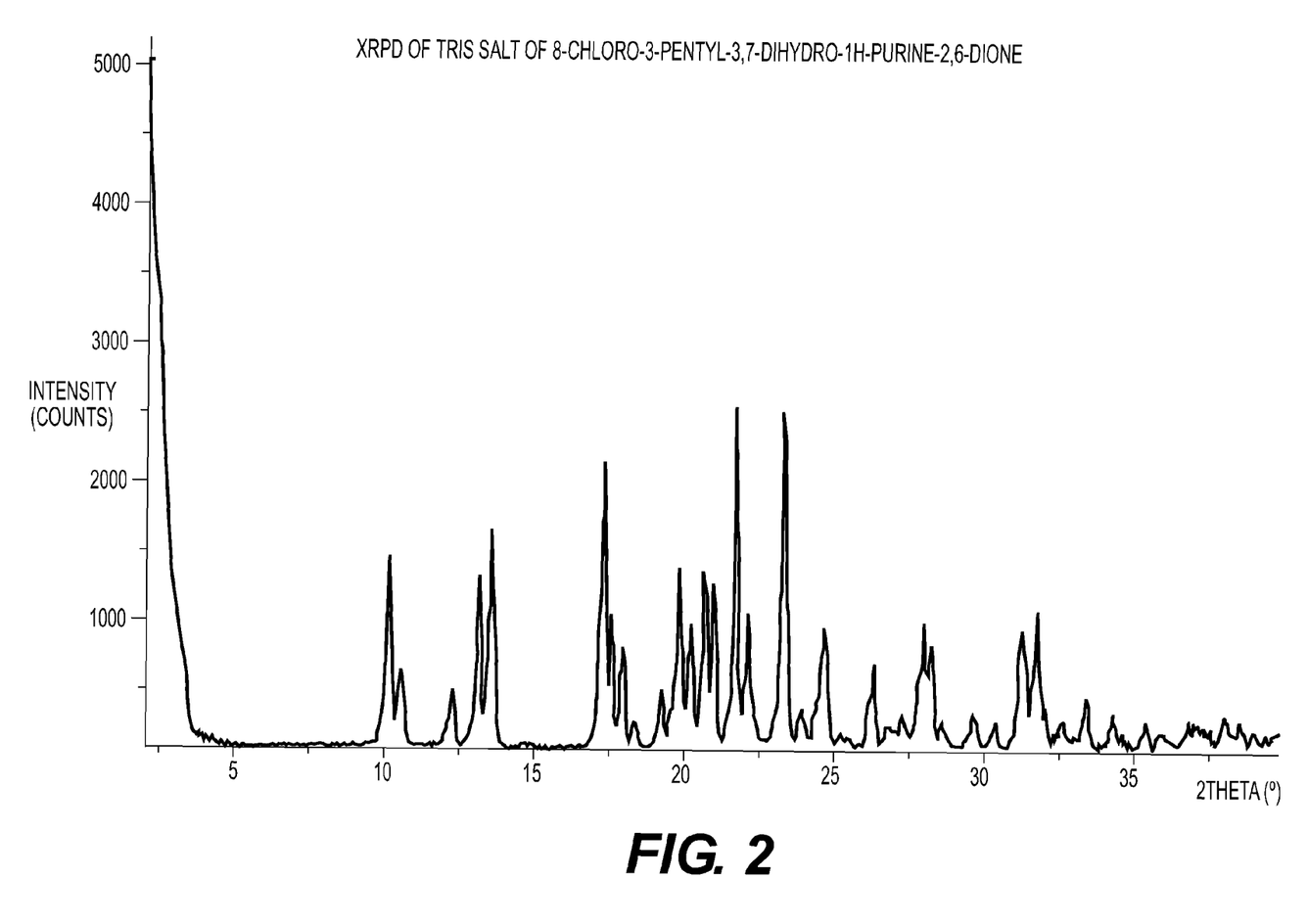
FIG. 2 shows an X-ray powder diffraction of the anhydrate form of the tris salt of 8-chloro-3-pentyl-3,7-dihydro-1H-purine-2,6-dione (Formula (IA)).
Figure 3:
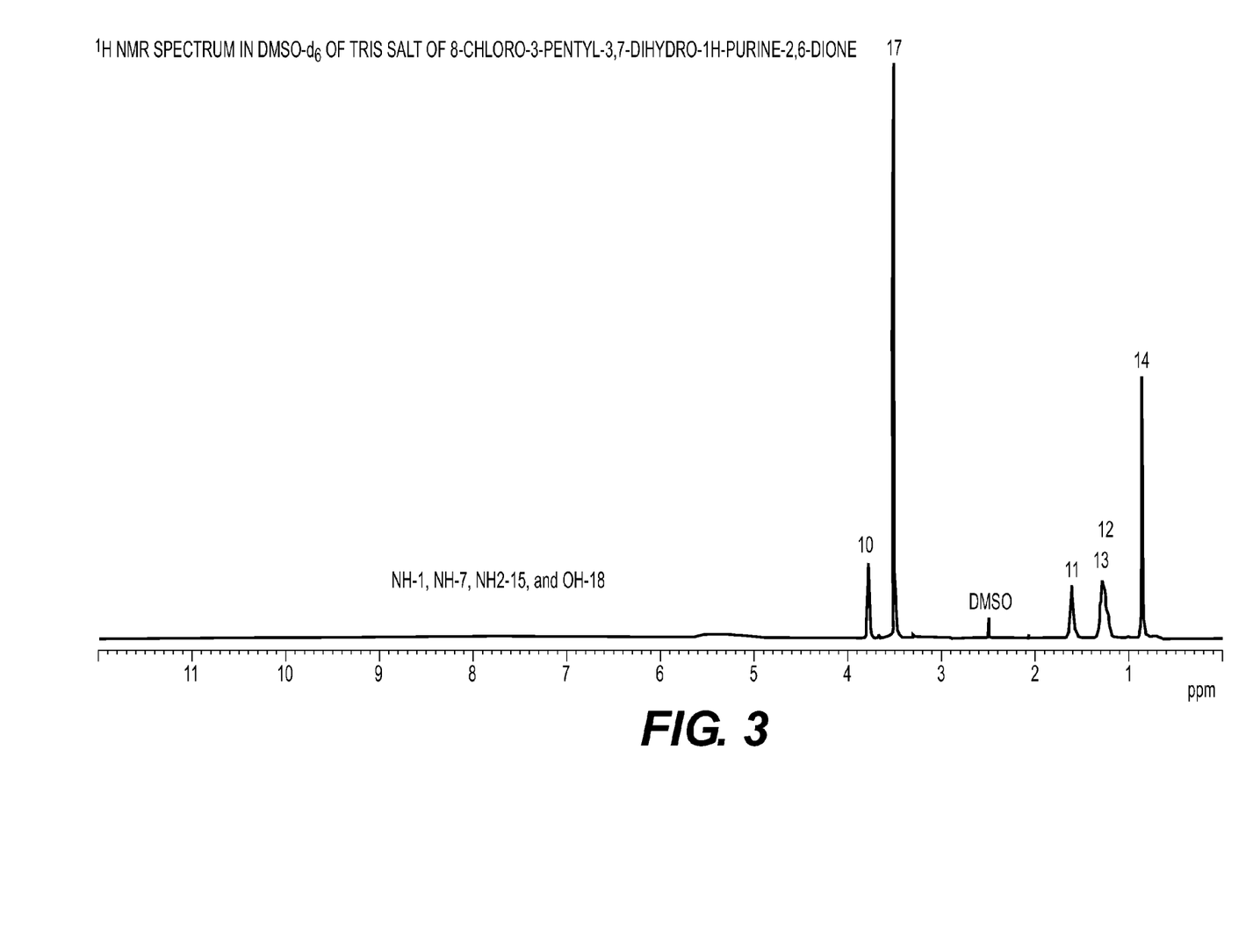
FIG. 3 shows an $^1$H NMR Spectrum of the anhydrate form of the tris salt of 8-chloro-3-pentyl-3,7-dihydro-1H-purine-2,6-dione (Formula (IA)).
Figure 4:
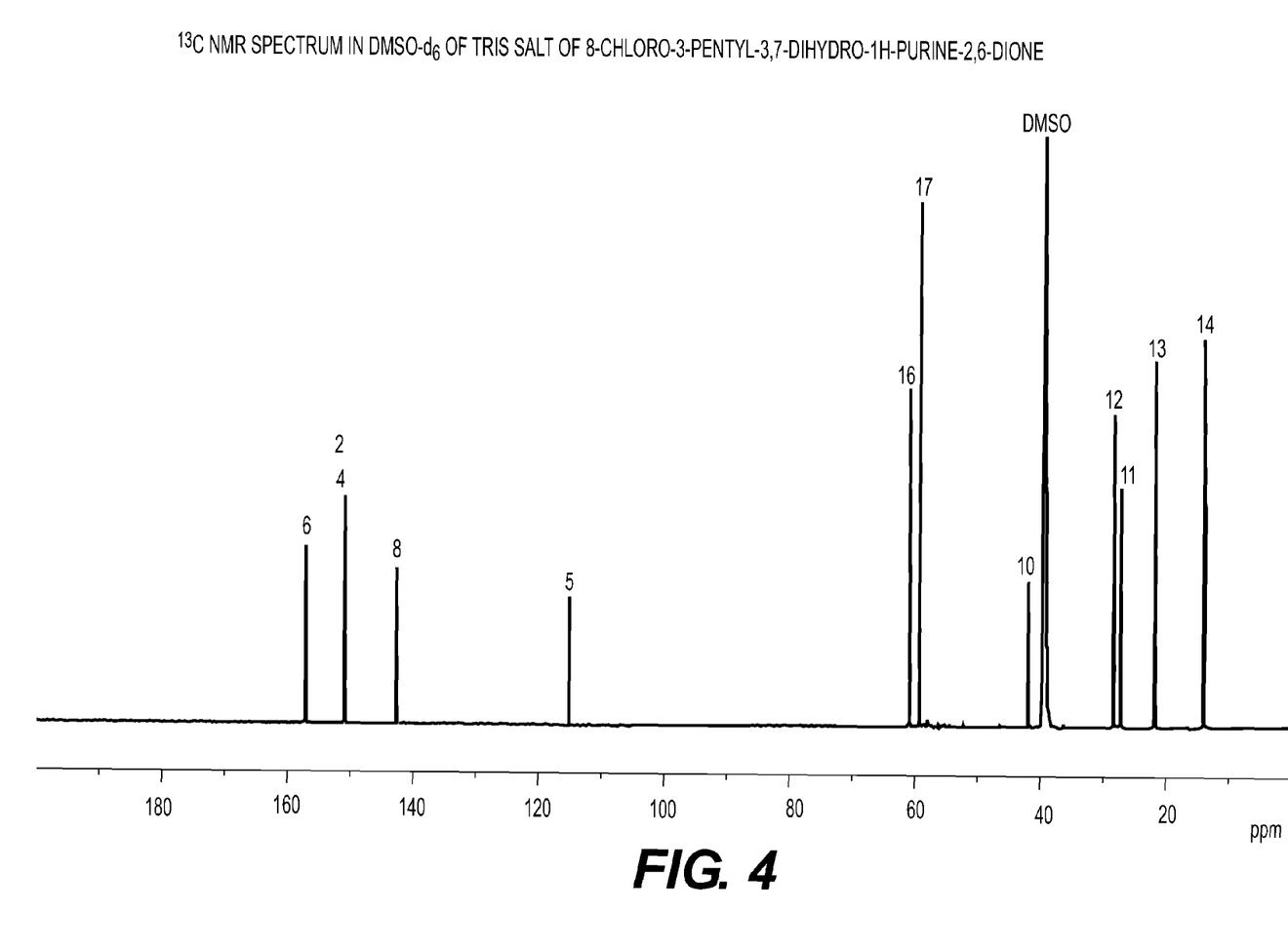
FIG. 4 shows an $^{13}$C NMR Spectrum of the anhydrate form of the tris salt of 8-chloro-3-pentyl-3,7-dihydro-1H-purine-2,6-dione (Formula (IA)).
Figure 5:
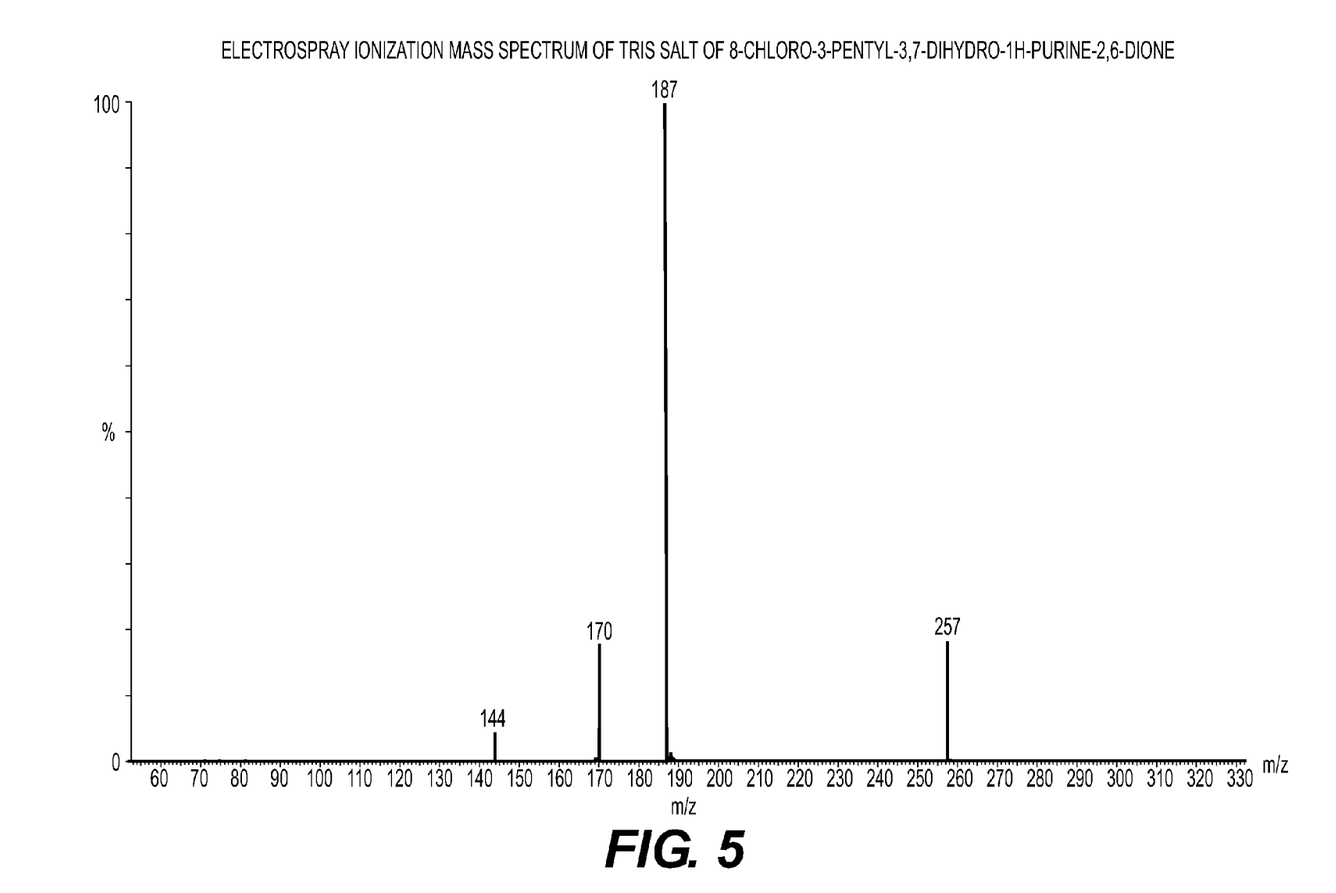
FIG. 5 shows an Electrospray Ionization Spectrum of the anhydrate form of the tris salt of 8-chloro-3-pentyl-3,7-dihydro-1H-purine-2,6-dione (Formula (IA))

In another aspect, the compound of Formula (IA) as an anhydrate in crystalline form is characterised by an XRPD pattern that is substantially as shown in FIG. 2.

In one aspect, the compound of Formula (IA) as an anhydrate in crystalline form is characterised by a melting endotherm with an onset melting temperature of 212±2° C. as determined by Differential Scanning calorimetry (DSC). Suitably by using an aluminium pan, lightly crimped without sealing and using a heating rate of 10° C. min$^{-1}$.

In one aspect, the compound of Formula (IA) as an anhydrate in crystalline form is characterised by the following absorption peaks in an Attenuated total reflection infrared (ATR-IR) spectrum of the solid product: 3370, 3041, 2946, 2858, 1680, 1656, 1528, 1266, 1243, 1078, 1068, 1049±1 cm-1.

Figure 6:
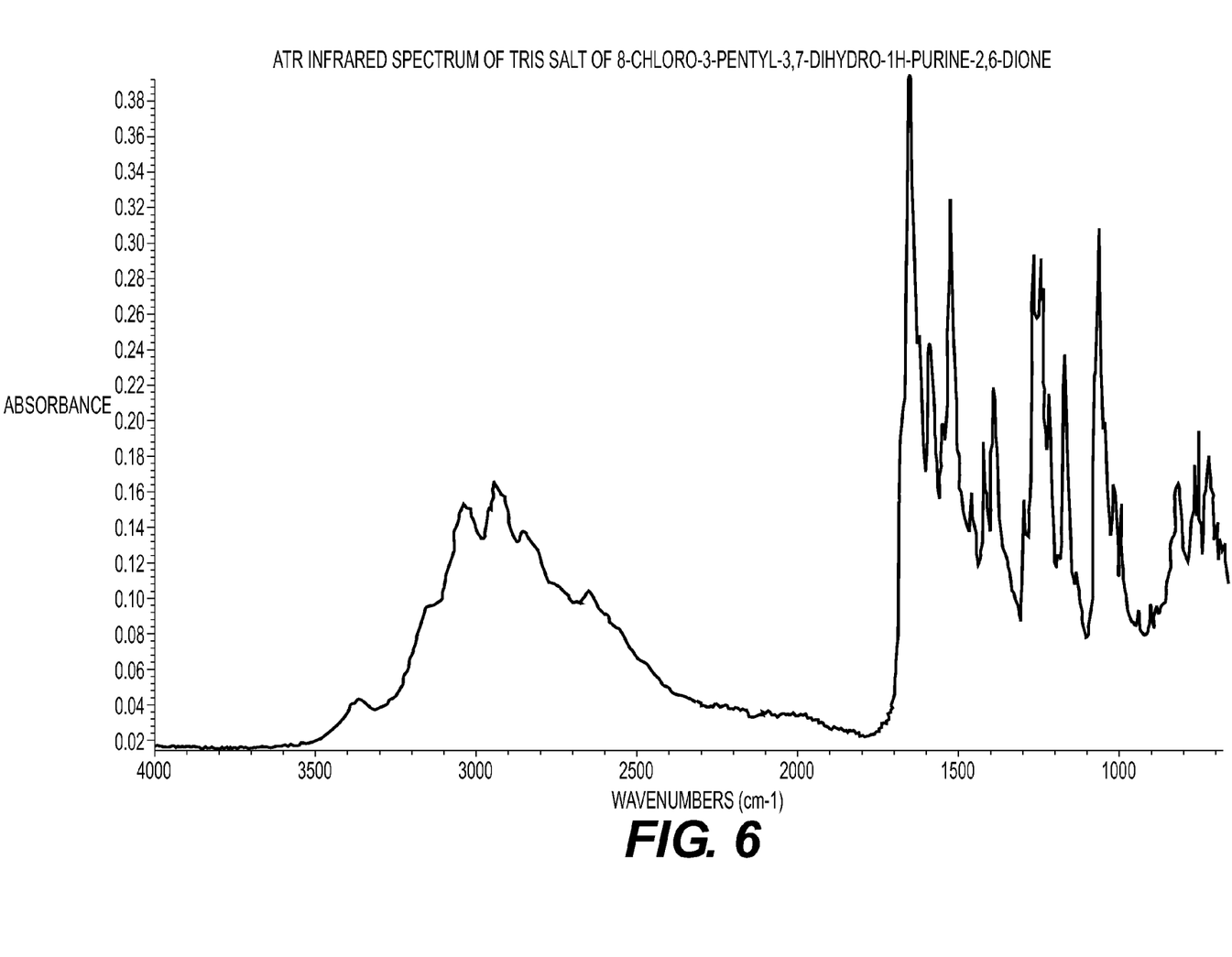
FIG. 6 shows an Attenuated total reflection (ATR) Infrared Spectrum of the anhydrate form of the tris salt of 8-chloro-3-pentyl-3,7-dihydro-1H-purine-2,6-dione (Formula (IA)).

In another aspect, the compound of Formula (IA) as an anhydrate in crystalline form is characterised in that it has an ATR-IR spectrum that is substantially as shown in FIG. 6.

As discussed and illustrated throughout, the present invention includes certain solid state crystalline forms. Several methods for characterizing such forms exist, and the invention should not be limited by the methods chosen or the instrumentation used in characterizing the compounds of the present invention. For example, with regard to x-ray diffraction patterns, the diffraction peak intensities in the experimental patterns can vary, as is known in the art, primarily due to preferred orientation (non-random orientation of the crystals) in the prepared sample. As such, the scope of the present invention must be considered in light of the variability of characterization that is appreciated by those skilled in the art.

In one aspect, the present invention relates to pharmaceutical compositions comprising the compound of Formula (IA).

In one aspect, the present invention relates to the use of the compound of Formula (IA) in therapy.

In another aspect, the present invention relates to the compound of Formula (IA) for use in the treatment of diseases where under-activation of the HM74A receptor contributes to the disease or where activation of the receptor will be beneficial, in particular dyslipidaemia, hyperlipoproteinaemia, diabetic dyslipidaemia, mixed dyslipidaemia, heart failure, hypercholesteraemia, cardiovascular disease, atherosclerosis, arteriosclerosis, hypertriglyceridaemia, Type II diabetes mellitus, Type I diabetes, insulin resistance, hyperlipidaemia, anorexia nervosa, obesity, coronary artery disease, thrombosis, angina, chronic renal failure, peripheral vascular disease or stroke.

In another aspect, the present invention relates to the use of the compound of Formula (IA) in the manufacture of a medicament for use in the treatment of diseases where under-activation of the HM74A receptor contributes to the disease or where activation of the receptor will be beneficial, in particular dyslipidaemia, hyperlipoproteinaemia, diabetic dyslipidaemia, mixed dyslipidaemia, heart failure, hypercholesteraemia, cardiovascular disease, atherosclerosis, arteriosclerosis, hypertriglyceridaemia, Type II diabetes mellitus, Type I diabetes, insulin resistance, hyperlipidaemia, anorexia nervosa, obesity, coronary artery disease, thrombosis, angina, chronic renal failure, peripheral vascular disease or stroke.

In another aspect, the present invention relates to methods of treating diseases where under-activation of the HM74A receptor contributes to the disease or where activation of the receptor will be beneficial, in particular dyslipidaemia, hyperlipoproteinaemia, diabetic dyslipidaemia, mixed dyslipidaemia, heart failure, hypercholesteraemia, cardiovascular disease, atherosclerosis, arteriosclerosis, hypertriglyceridaemia, Type II diabetes mellitus, Type I diabetes, insulin resistance, hyperlipidaemia, anorexia nervosa, obesity, coronary artery disease, thrombosis, angina, chronic renal failure, peripheral vascular disease or stroke, comprising administration of a therapeutically effective amount of the compound of Formula (IA).

DETAILED DESCRIPTION OF THE INVENTION

Throughout the present specification and the accompanying claims the words "comprise" and variations such as "comprises", "comprising" are to be interpreted inclusively. That is, these words are intended to convey the possible inclusion of other elements or integers not specifically recited, where the context allows.

As used herein, the term "therapeutically effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein, the term "pharmaceutically acceptable" means a compound which is suitable for pharmaceutical use. Solvates of the compound of Formula (IA) which are suitable for use in medicine are those wherein the counterion or associated solvent is pharmaceutically acceptable.

As used herein, the terms "treating" or "treatment" means the alleviation of the symptoms and/or retardation of progression of the disease, and may include the suppression of symptom recurrence in an asymptomatic patient.

Reference to the compound of Formula (IA) encompasses solvates (e.g. hydrates) of the compound.

Those skilled in the art of organic chemistry will appreciate that many organic compounds can form complexes with solvents in which they are reacted or from which they are precipitated or crystallized.

Solvates of the compound of Formula (IA) are included within the scope of the present invention. As used herein, the term "solvate" refers to a complex of variable stoichiometry formed by a solute (the compound of Formula (IA)) and a solvent. Such solvents for the purpose of the invention may not interfere with the biological activity of the solute. Examples of suitable solvents include, but are not limited to, water, methanol, ethanol and acetic acid and the like.

In one aspect, suitable solvent(s) for use in the present invention is/are pharmaceutically acceptable solvent(s). Examples of suitable pharmaceutically acceptable solvents include, without limitation, water, ethanol and acetic acid and the like. As used herein, the term "hydrate" refers to a complex of variable stoichiometry formed with or in the presence of water. In one aspect of the present invention, the solvent used is water.

Because of its potential use in medicine, in one aspect the tris salt of 8-chloro-3-pentyl-3,7-dihydro-1H-purine-2,6-dione (Formula (IA)) will be pharmaceutically acceptable. The invention includes within its scope all possible stoichiometric and non-stoichiometric forms of the compound of Formula (IA).

In one aspect, the present invention relates to the tris salt form of 8-chloro-3-pentyl-3,7-dihydro-1H-purine-2,6-dione (Formula (IA)), which may include solvates or hydrates thereof.

There is provided as a further aspect of the present invention the use of the compound of Formula (IA), in the manufacture of a medicament for use in the treatment of dyslipidaemia, hyperlipoproteinaemia, diabetic dyslipidaemia, mixed dyslipidaemia, heart failure, hypercholesteraemia, cardiovascular disease, atherosclerosis, arteriosclerosis, hypertriglyceridaemia, Type II diabetes mellitus, Type I diabetes, insulin resistance, hyperlipidaemia, anorexia nervosa and obesity. As such, the compounds are also provided for use in the treatment of coronary artery disease, thrombosis, angina, chronic renal failure, peripheral vascular disease or stroke.

Additionally, the present invention provides the use of the compound of Formula (IA), in the manufacture of a medicament for use in the treatment of inflammatory diseases or conditions of the joint, particularly arthritis (e.g. rheumatoid arthritis, osteoarthritis, prosthetic joint failure), or of the gastrointestinal tract (e.g. ulcerative colitis, Crohn's disease, and other inflammatory bowel and gastrointestinal diseases, gastritis and mucosal inflammation resulting from infection, the enteropathy provoked by non-steroidal anti-inflammatory drugs), of the lung (e.g. adult respiratory distress syndrome, asthma, cystic fibrosis, or chronic obstructive pulmonary disease), of the heart (e.g. myocarditis), of nervous tissue (e.g. multiple sclerosis), of the pancreas, (e.g. inflammation associated with diabetes melitus and complications thereof, of the kidney (e.g. glomerulonephritis), of the skin (e.g. dermatitis, psoriasis, eczema, urticaria, burn injury), of the eye (e.g. glaucoma) as well as of transplanted organs (e.g. rejection) and multi-organ diseases (e.g. systemic lupus erythematosis, sepsis) and inflammatory sequelae of viral or bacterial infections and inflammatory conditions associated with atherosclerosis and following hypoxic or ischaemic insults (with or without reperfusion), for example in the brain or in ischaemic heart disease.

In a further or alternative aspect there is provided a method for the treatment of a human subject with a condition where under-activation of the HM74A receptor contributes to the condition or where activation of the receptor will be beneficial, which method comprises administering to said human subject an effective amount of the compound of Formula (IA).

More particularly, the present invention provides a method for the treatment of dyslipidaemia, hyperlipoproteinaemia, diabetic dyslipidaemia, mixed dyslipidaemia, heart failure, hypercholesteraemia, cardiovascular disease, atherosclerosis, arteriosclerosis, hypertriglyceridaemia, Type II diabetes mellitus, Type I diabetes, insulin resistance, hyperlipidaemia, anorexia nervosa or obesity, in a human subject in need thereof, which method comprises administering to said human subject an therapeutically effective amount of a compound of Formula (IA).

As such, these compounds may also find favour in methods for the treatment of coronary artery disease, thrombosis, angina, chronic renal failure, peripheral vascular disease or stroke, which methods comprise administering to said human subject an therapeutically effective amount of the compound of Formula (IA).

The amount of the compound of Formula (IA) which is required to achieve the desired biological effect will, of course, depend on a number of factors, for example, the mode of administration and the precise clinical condition of the recipient. In general, the daily dose will be in the range of 1 mg to 500 mg, typically 5 mg to 250 mg or 5 mg to 200 mg. For example, 7.35 mg, 36.75 mg, 73.5 mg or 147 mg (equiv to 5 mg, 25 mg, 50 mg and 100 mg of free acid). An intravenous dose may, for example, be in the range of 0.01 mg to 0.1 g, typically 0.01 mg to 10 mg, which may conveniently be administered as an infusion of from 0.1 µg to 1 mg, per minute. Infusion fluids suitable for this purpose may contain, for example, from 0.01 µg to 0.1 mg, per millilitre. Unit doses may contain, for example, from 0.01 µg to 1 g of tris salt. Thus ampoules for injection may contain, for example, from 0.01 µg to 0.1 g and orally administrable unit dose formulations, such as tablets or capsules, may contain, for example, from 0.1 mg to 1 g. No toxicological effects are indicated/expected when a compound of the invention is administered in the above mentioned dosage range.

Pharmaceutical Compositions

While it is possible that, for use in the methods of the invention, the compound of formula (IA) may be administered as the bulk substance, it is preferable to present the active ingredient in a pharmaceutical formulation, for example, wherein the agent is in admixture with at least one pharmaceutically acceptable carrier selected with regard to the intended route of administration and standard pharmaceutical practice.

The invention therefore provides a pharmaceutical composition comprising the compound of Formula (IA), in association with one or more pharmaceutically acceptable carrier(s), diluents(s) and/or excipient(s). The carrier, diluent and/or excipient must be "acceptable" in the sense of being compatible with the other ingredients of the composition and not deleterious to the recipient thereof.

Accordingly, the present invention provides a pharmaceutical composition comprising a) the compound of Formula (IA) and b) one or more pharmaceutically acceptable carriers.

The term "carrier" refers to a diluent, excipient, and/or vehicle with which an active compound is administered. The pharmaceutical compositions of the invention may contain combinations of more than one carrier. Such pharmaceutical carriers can be sterile liquids, such as water, saline solutions, aqueous dextrose solutions, aqueous glycerol solutions, and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin, 18th Edition. The choice of pharmaceutical carrier can be selected with regard to the intended route of administration and standard pharmaceutical practice. The pharmaceutical compositions may comprise as, in addition to, the carrier any suitable binder(s), lubricant(s), suspending agent(s), coating agent(s), and/or solubilizing agent(s).

The formulations include those suitable for oral, rectal, topical, buccal (e.g. sub-lingual) and parenteral (e.g. subcutaneous, intramuscular, intradermal or intravenous) administration. The most preferred form of administration is oral.

Formulations suitable for oral administration may be presented in discrete units, such as capsules, cachets, lozenges or tablets, each containing a predetermined amount of the compound of Formula (IA); as a powder or granules; as a solution or a suspension in an aqueous or non-aqueous liquid; or as an oil-in-water or water-in-oil emulsion. In general, the formulations are prepared by uniformly and intimately admixing the active compound of Formula (IA) with a liquid or finely divided solid carrier, or both, and then, if necessary, shaping the product. For example, a tablet may be prepared by compressing or moulding a powder or granules of the compound of Formula (IA) optionally with one or more accessory ingredients. Compressed tablets may be prepared by compressing, in a suitable machine, the compound in a free-flowing form, such as a powder or granules optionally mixed with a binder, lubricant, inert diluent and/or surface active/dispersing agent(s). Moulded tablets may be made by moulding, in a suitable machine, the powdered compound moistened with an inert liquid diluent.

Tablets and capsules for oral administration may contain conventional excipients such as binding agents, for example syrup, acacia, gelatin, sorbitol, tragacanth, mucilage of starch or polyvinyl pyrrolidone; fillers, for example, lactose, microcrystalline cellulose, sugar, maize-starch, calcium phosphate or sorbitol; lubricants, for example, magnesium stearate, stearic acid, talc, polyethylene glycol or silica; disintegrants, for example, potato starch, croscarmellose sodium or sodium starch glycollate; or wetting agents such as sodium lauryl sulphate. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, for example, sorbitol syrup, methyl cellulose, glucose/sugar syrup, gelatin, hydroxymethyl cellulose, carboxymethyl cellulose, aluminium stearate gel or hydrogenated edible fats; emulsifying agents, for example, lecithin, sorbitan mono-oleate or acacia; non-aqueous vehicles (which may include edible oils), for example almond oil, fractionated coconut oil, oily esters, propylene glycol or ethyl alcohol; or preservatives, for example, methyl or propyl p-hydroxybenzoates or sorbic acid. The preparations may also contain buffer salts, flavouring, colouring and/or sweetening agents (e.g. mannitol) as appropriate.

Formulations suitable for buccal (sub-lingual) administration include lozenges comprising the compound of Formula (IA) in a flavoured base, usually sucrose and acacia or tragacanth, and pastilles comprising the compound of Formula (IA) in an inert base such as gelatin and glycerin or sucrose and acacia.

Formulations of the present invention suitable for parenteral administration conveniently comprise sterile aqueous preparations of the compound of Formula (IA) the formulation may be isotonic with the blood of the intended recipient. These preparations could be administered intravenously, although administration may also be effected by means of subcutaneous, intramuscular, or intradermal injection. Such preparations may conveniently be prepared by admixing the compound of Formula (IA) with water and rendering the resulting solution sterile and isotonic with the blood. Injectable compositions according to the invention will generally contain from 0.1 to 5% w/w of the compound of Formula (IA).

Thus, formulations of the present invention suitable for parenteral administration comprising a compound according to the invention may be formulated for parenteral administration by bolus injection or continuous infusion and may be presented in unit dose form, for instance as ampoules, vials, small volume infusions or pre-filled syringes, or in multi-dose containers with an added preservative. The compositions may take such forms as solutions, suspensions, or emulsions in aqueous or non-aqueous vehicles, and may contain formulatory agents such as anti-oxidants, buffers, antimicrobial agents and/or toxicity adjusting agents. Alternatively, the active ingredient may be in powder form for constitution with a suitable vehicle, e.g. sterile, pyrogen-free water, before use. The dry solid presentation may be prepared by filling a sterile powder aseptically into individual sterile containers or by filling a sterile solution aseptically into each container and freeze-drying.

Formulations suitable for rectal administration may be presented as unit-dose suppositories. These may be prepared by admixing the compound of Formula (IA) with one or more conventional solid carriers, for example, cocoa butter or glycerides and then shaping the resulting mixture.

Formulations suitable for topical application to the skin may take the form of an ointment, cream, lotion, paste, gel, spray, aerosol, or oil. Carriers which may be used include vaseline, lanolin, polyethylene glycols, alcohols, and combinations of two or more thereof. The compound of Formula (IA) is generally present at a concentration of from 0.1 to 15% w/w of the composition, for example, from 0.5 to 2%.

By topical administration as used herein, we include administration by insufflation and inhalation. Examples of various types of preparation for topical administration include ointments, creams, lotions, powders, pessaries, sprays, aerosols, capsules or cartridges for use in an inhaler or insufflator or drops (e.g. eye or nose drops).

Ointments and creams may, for example, be formulated with an aqueous or oily base with the addition of suitable thickening and/or gelling agents and/or solvents. Such bases may thus, for example, include water and/or an oil such as liquid paraffin or a vegetable oil such as arachis oil or castor oil or a solvent such as a polyethylene glycol. Thickening agents which may be used include soft paraffin, aluminium stearate, cetostearyl alcohol, polyethylene glycols, microcrystalline wax and beeswax.

Lotions may be formulated with an aqueous or oily base and will in general also contain one or more emulsifying agents, stabilising agents, dispersing agents, suspending agents or thickening agents.

Powders for external application may be formed with the aid of any suitable powder base, for example, talc, lactose or starch. Drops may be formulated with an aqueous or non-aqueous base also comprising one or more dispersing agents, solubilising agents or suspending agents.

Spray compositions may be formulated, for example, as aqueous solutions or suspensions or as aerosols delivered from pressurised packs, with the use of a suitable propellant, e.g. dichlorodifluoromethane, trichlorofluoromethane, dichlorotetrafluoroethane, 1,1,1,2,3,3,3-heptafluoropropane, 1,1,1,2-tetrafluorethane, carbon dioxide or other suitable gas.

Capsules and cartridges for use in an inhaler or insufflator, of for example gelatin, may be formulated containing a powder mix of a compound of the invention and a suitable powder base such as lactose or starch.

The pharmaceutical compositions according to the invention may also be used in combination with other therapeutically active agents, for example in combination with other classes of dyslipidaemic drugs (e.g. statins, fibrates, bile-acid binding resins or nicotinic acid).

The compound of Formula (IA) may be used in combination with one or more other therapeutically active agents for example in combination with other classes of dyslipidaemic drugs e.g. 3-hydroxy-3-methylglutaryl-coenzyme A reductase inhibitors (statins) or fibrates or bile acid binding resins or nicotinic acid.

In one aspect, the present invention provides a combination comprising a) a compound of Formula (IA) and b) one or more therapeutically active agents.

The invention thus provides, in a further aspect, the use of such a combination in the treatment of diseases where under-activation of the HM74A receptor contributes to the disease or where activation of the receptor will be beneficial and the use of the compound of formula (IA) in the manufacture of a medicament for the combination therapy of dyslipidaemia, hyperlipoproteinaemia, diabetic dyslipidaemia, mixed dyslipidaemia, heart failure, hypercholesteraemia, cardiovascular disease, atherosclerosis, arteriosclerosis, and hypertriglyceridaemia, Type II diabetes mellitus, Type I diabetes, insulin resistance, hyperlipidaemia, anorexia nervosa or obesity.

When the compounds of the present invention are used in combination with other therapeutic agents, the compounds may be administered either sequentially or simultaneously by any convenient route.

The combinations referred to above may conveniently be presented for use in the form of a pharmaceutical formulation and thus pharmaceutical formulations comprising a combination as defined above optimally together with a pharmaceutically acceptable carrier or excipient comprise a further aspect of the invention. The individual components of such combinations may be administered either sequentially or simultaneously in separate or combined pharmaceutical formulations.

When combined in the same formulation it will be appreciated that the two components must be stable and compatible with each other and the other components of the formulation and may be formulated for administration. When formulated separately they may be provided in any convenient formulation, conveniently in such a manner as are known for such compounds in the art.

When in combination with a second therapeutic agent active against the same disease, the dose of each component may differ from that when the compound is used alone. Appropriate doses will be readily appreciated by those skilled in the art.

The invention thus provides, in a further aspect, a combination comprising the compound of Formula (IA) together with another therapeutically active agent. An example of another therapeutically active agent being Niacin or Atorvastatin sodium.

The combination referred to above may conveniently be presented for use in the form of a pharmaceutical formulation and thus pharmaceutical formulations comprising a combination as defined above together with a pharmaceutically acceptable carrier thereof represent a further aspect of the invention.

The compounds of the present invention have a useful duration of action.

Methods of Preparation

The present invention further provides a process for preparing the tris salt of 8-chloro-3-pentyl-3,7-dihydro-1H-purine-2,6-dione as shown in Scheme 1 below.

Scheme 1:

-continued

Stage 3: NCS / DMF

Stage 4: H₃C(CH₂)₄—X / Base, DMF

Stage 5: Pd(PPh₃)₄

Formula A

Stages 1, 2 3, 4 and 5 are as described in WO2005/077950, which is incorporated by reference by its entirety.
Stage 1: Alkylation of guanosine with allyl bromide
Stage 2: Diazotisation with sodium nitrite followed by hydrolysis to form the xanthine
Stage 3: Chlorination
Stage 4: Alkylation at N3 and/or dialkylation at N1 and N3
Stage 5: Palladium catalysed removal of the allyl group
Alternatively, stage 5 may also be carried out by deprotection with dimethylbarbituric acid.
The final stage in the preparation of the tris salt is combining a compound of formula (A) with trishydroxymethylaminomethane as shown below:

Formula (A)

Formula (IA)

The Examples set forth below are illustrative of the present invention and are not intended to limit in any way, the scope of the present invention.

EXAMPLES

Example 1

Preparation of 8-Chloro-3-Pentyl-3,7-Dihydro-1H-Purine-2,6-Dione Tris Hydroxyl Methyl Aminomethane Salt (i.e., Also Known As 8-Chloro-3-Pentyl-3,7-Dihydro-1H-Purine-2,6-Dione-2-Amino-2-(Hydroxymethyl)-1,3-Propanediol (I.E., IUPAC).

A slurry was formed of 1.0 gram of 8-chloro-3-pentyl-3,7-dihydro-1H-purine-2,6-dione in 10 volumes of acetonitrile to which 1.1 equivalents of tris(hydroxymethyl)aminomethane was added in 1.2 volumes of water. The reaction mixture was heated to reflux at approx. 75 to 77° C., which dissolved the aforementioned components. Initial dissolution of components was followed by rapid spontaneous crystal formation. Crystals of 8-chloro-3-pentyl-3,7-dihydro-1H-purine-2,6-dione tris hydroxylmethyl aminomethane salt were isolated by filtration (Product Yield: 94%).

Example 2

Preparation of 8-Chloro-3-Pentyl-3,7-Dihydro-1H-Purine-2,6-Dione Tris Hydroxyl Methyl Aminomethane Salt A slurry was formed of 8-chloro-3-pentyl-3,7-dihydro-1H-purine-2,6-dione (22 kg, contains approximately 16% water) and acetone (125 L) to which a solution of tris(hydroxymethyl)aminomethane (9.3 kg) in water (79.8 kg) was added at room temperature. After heating to near reflux temperature to approximately 55° C., the solution was filtered through a 1.2 micron filter cartridge at 55° C. and the batch temperature was adjusted to 61 to 63° C. After holding for 30 min, the solution was cooled to 53 to 57° C. and seeded with seed crystals (0.062 kg), which were made in the same way from an acetone water crystallisation or, as obtained such as, or from a procedure of Example 1 above, as a slurry in acetone (2 L). In the process, the crystallisation is seeded in order to provide control of particle size and to ensure the desired product form was obtained.

The mixture was stirred at 53 to 57° C. for 1 hour. The resulting slurry was then slowly cooled with stirring to 18 to 22° C. and acetone (75 L) was charged over 30 minutes. After stirring at 18 to 22° C. for 30 minutes, the resulting slurry was cooled to −5 to 0° C., held for 18 hours, filtered, and washed with pre-cooled (−5 to 0° C.) acetone (75 L). The resulting 8-chloro-3-pentyl-3,7-dihydro-1H-purine-2,6-dione tris hydroxylmethyl aminomethane salt was dried at 45 to 50° C. under vacuum. Yield: 18.2 kg (67% yield).

Example 3

Preparation of
8-Chloro-3-Pentyl-3,7-Dihydro-1H-Purine-2,6-Dione
Tris Hydroxyl Methyl Aminomethane Salt 8-Chloro-3-pentyl-3,7-dihydro-1H-purine-2,6-dione (29 kg) was dissolved in DMSO (40 L) at an elevated temperature of approx. 90 to 100° C. and filtered through a 5 micron filter, followed by a DMSO (13 L) line wash. Tris(hydroxymethyl) aminomethane (15.1 kg) was dissolved in water (44 L) and filtered through a 5 micron filter into the same vessel as the parent acid, followed by a water (15 L) line wash. The contents of the vessel were then heated to approximately 95° C. to ensure a clear solution was obtained. Contents were cooled to 88° C. and seeded with seed crystals, where the seed crystals, made in same way from an acetone water crystallisation or, as obtained such as, or from a procedure of Example 1 above. In this process, the crystallisation is seeded in order to provide control of particle size and to ensure the desired product form was obtained. The seeded slurry was held for approximately 30 minutes and cooled to 0° C. The product was isolated by filtration, washed with ~5° C. DMSO/water (1:1, 58 L) and ~5° C. acetone (2×58 L). The resulting product was dried at 50° C. under vacuum. Yield: 35.4 kg (83% yield)

Example 4

Preparation of
8-Chloro-3-Pentyl-3,7-Dihydro-1H-Purine-2,6-Dione
Tris Hydroxyl Methyl Aminomethane Salt
Formulation

| Component | Quantity (mg/tablet) | | |
|---|---|---|---|
| | 25 mg | 50 mg | 100 mg |
| Granulation | | | |
| Tris salt[1] | 36.75 | 73.50 | 147.00 |
| Mannitol Powder | 9.25 | 18.50 | 37.00 |
| Povidone | 2.50 | 5.00 | 10.00 |
| Crospovidone | 1.50 | 3.00 | 6.00 |
| Purified Water[2] | q.s. | q.s. | q.s. |
| Compression Blend | | | |
| Microcrystalline Cellulose | 338.00 | 280.00 | 172.00 |
| Crospovidone | 8.00 | 16.00 | 24.00 |
| Magnesium Stearate[3] | 4.00 | 4.00 | 4.00 |
| Aqueous Film Coating | | | |
| Opadry White OY-S-9603 | 12.00 | 12.00 | 12.00 |
| Purified Water[2] | q.s. | q.s. | q.s. |
| Tablet Weight | 412.00 | 412.00 | 412.00 |

[1]An amount of 36.75 mg, 73.50 mg or 147.00 mg of Tris salt is required to achieve the 25 mg, 50 mg or 100 mg free acid respectively, calculated by a conversion factor of 1.47. The amount of drug substance may be adjusted based on the purity assay.
[2]Water is removed during processing.
[3]Vegetable source.

The tris salt, mannitol powder, povidone, crospovidone and purified water were granulated by utilising a fluid bed granulator. The fluid bed was then dried. The granulation was then blended with microcrystalline cellulose, crospovidone and magnesium stearate and compressed on a tablet press. The resulting tablets were then covered in an aqueous film coating of opadry and water.

Povidone (polyvinylpyrrolidone) is a synthetic polymer consisting of linear 1-vinyl-2-pyrrolidone groups and mean molecular weights ranging from about 10,000 to about 700,000 supplied by BASF Chemicals. Povidone is used as a binder during the granulation process.

Crospovidone is a crosslinked povidone, and is a water-insoluble tablet disintegrant and dissolution agent used at 2 to 5% concentration in tablets. It is supplied by BASF Chemicals.

Opadry White OY-S-9603 is a proprietary film-coating material supplied by Colorcon. Reference is made to the Colorcon Drug Master File Number 721 for the manufacturing and control of Opadry White OY-S-9603 Aqueous Film Coating.

According to the instant invention, the various forms of compounds of the present invention (i.e. which include solvates thereof) are distinguished from each other using different characterization or identification techniques. Such techniques, include solid state $^{13}$C Nuclear Magnetic Resonance (NMR), $^{31}$P Nuclear Magnetic Resonance (NMR), Infrared (IR), Raman, X-ray powder diffraction, etc. and/or other techniques, such as Differential Scanning calorimetry (DSC) (i.e., which measures the amount of energy (heat) absorbed or released by a sample as it is heated, cooled or held at constant temperature).

Specifically, the tris salt of the present invention is substantially as shown by the data described in FIGS. 1 to 6.

The following characterizing data were generated for the trishydroxymethyl amino methane (tris) salt of 8-chloro-3-pentyl-3,7-dihydro-1H-purine-2,6-dione of the present invention (Formula (IA)).

It will be recognised that spectra and diffraction data will vary slightly according to various factors such as the temperature, concentration and instrumentation used.

Example 5

UV/Visible Absorption Spectrum

The UV/Visible Absorption Spectrum was obtained in acetonitrile:water, 95:5. A 0.02 mg/ml sample of the tris salt was prepared and analysed with a 1 cm path length. Spectra were accumulated at a scan rate of 300 nm/min on a Varian Cary 50 spectrometer.

| Absorbance maxima (nm), $\lambda_{max}$ | Molar Absorption Coefficient, ($\epsilon$) |
|---|---|
| 278 | 12500 |
| 206 | 20700 |

Example 6

Differential Scanning Calorimetry (DSC): Melting Point

The melting point or thermal behaviour of the tris salt of the present invention was investigated with differential scanning calorimetry (DSC). The onset of melting is typically observed at 212° C.±2° C.

The DSC trace was obtained using a TA Q1000 calorimeter. The sample was weighed into an aluminium pan, a pan lid placed on top and lightly crimped without sealing the pan. The experiment was conducted using a heating rate of 10° C. min$^{-1}$.

Example 7 and 8

$^1$H and $^{13}$C Nuclear Magnetic Resonance Spectra $^1$H NMR spectra were acquired on a 400 MHz Varian spectrometer at 298K. Sample was dissolved in DMSO-d$_6$ and chemical shifts were reported in ppm relative to the tetramethylsilane (TMS) signal at 0 ppm. Coupling constants (J) are in units of hertz (Hz). Splitting patterns describe apparent multiplicities and are designated as s (singlet), d (doublet), t (triplet), q (quartet), dd (double doublet), dt (double triplet), m (multiplet), br (broad).

$^1$H NMR (400 MHz, DMSO-d$_6$) δ ppm: 10.07-5.41 (br, 7H), 3.80 (t, 2H), 3.52 (s, 6H), 1.61 (m, 2H), 1.29 (m, 1H), 1.28 (m, 2H), 0.86 (t, 3H)

$^{13}$C NMR spectra were acquired on a 100 MHz Varian spectrometer at 298 K. Sample was dissolved in DMSO-d$_6$ and chemical shifts were reported relative to the TMS signal at 0 ppm.

$^{13}$C NMR (100 MHz, DMSO-d$_6$, 25 mg/mL 25° C.) δ ppm: 157.0, 151.0, 150.9, 142.8, 115.2, 61.0, 59.4, 42.0, 28.4, 27.3, 22.0, 13.9

Example 9

Positive Ion Electrospray Ionization Mass Spectrum

Mass spectra were collected on a Q-TOF Premier LC-MS. Samples were dissolved in acetonitrile/water and ionized by electrospray ionization. The desolvation gas temperature was at 350° C. and the desolvation gas flow rate was 600 L/hr. The spray voltage was 3.5 kV and the source temperature was maintained at 120° C. The collision gas flow rate was 0.5 ml/min.

The accurate mass of the protonated molecule was measured at 257.0804 Da. The calculated mass of this ion is 257.0805 Da.

MS (m/z): 257.0804 Da [M+H]$^+$: 187, 170, 144 (measurement accords with elemental composition of this ion with an error of 0.3 ppm)

Example 10

Infrared Spectrum (IR)

ATR Infrared spectrum: Peak Wavenumber (cm$^{-1}$) 3370, 3041, 2946, 2858, 1680, 1656, 1528, 1266, 1243, 1078, 1068, 1049.

The DATR infra red spectrum was acquired after 128 scans at 4 cm-1 resolution on a SensIR Travel IR DATR.

Example 11

X-Ray Powder Diffraction (XRPD)

The tris salt of 8-chloro-3-pentyl-3,7-dihydro-1H-purine-2,6-dione of the present invention is crystalline as indicated by X-ray powder diffraction (XRPD) data and is as shown in FIG. 2.

The X-ray powder diffractogram (XRPD) shown in FIG. 2 was obtained on a PANalytical X'Pert Pro powder diffractometer fitted with an X'Celerator detector and utilising a fixed divergence slit. The acquisition conditions were: radiation: Cu Kα, generator tension: 40 kV, generator current 40 mA, start angle: 2.0° 2θ, end angle 40° 2θ, step size 0.017° 2θ. The sample was spun during data acquisition. Characteristic XRPD angles and d-spacings are recorded in Table 1.

TABLE 1

Characteristic XRPD peak angles and d-spacings
The skilled person will recognise that XRPD peak positions are affected by differences in sample height. The peak positions quoted herein are thus subject to a variation of +/−0.2 degrees 2-theta.

| Position (±0.2° 2-theta) | d-spacing ((Å)) |
| --- | --- |
| 10.1 | 8.7 |
| 10.5 | 8.4 |
| 12.2 | 7.3 |
| 13.0 | 6.8 |
| 13.5 | 6.5 |
| 17.3 | 5.1 |
| 17.5 | 5.1 |
| 17.9 | 5.0 |
| 18.3 | 4.8 |
| 19.2 | 4.6 |
| 19.8 | 4.5 |
| 20.2 | 4.4 |
| 20.6 | 4.3 |
| 20.9 | 4.2 |
| 21.7 | 4.1 |
| 22.1 | 4.0 |
| 23.3 | 3.8 |
| 23.9 | 3.7 |
| 24.6 | 3.6 |
| 26.3 | 3.4 |
| 27.1 | 3.3 |
| 27.9 | 3.2 |
| 28.2 | 3.2 |
| 28.6 | 3.1 |
| 29.6 | 3.0 |

Example 12

Elemental Analysis

The stoichiometry of the tromethamine (tris) salt is confirmed by the elemental analysis data presented, which is in agreement with the theoretical values for the corresponding molecular formula.

| Molecular Formula | $C_{(14)}H_{(24)}N_{(5)}S_{(0)}$ | |
| --- | --- | --- |
| Element | % w/w Theoretical | % w/w Found |
| C | 44.5 | 44.7 |
| H | 6.4 | 6.3 |
| N | 18.5 | 18.5 |

It is to be understood that the invention is not limited to the embodiments illustrated hereinabove and the right is reserved to the illustrated embodiments and all modifications coming within the scope of the following claims.

The various references to journals, patents, and other publications which are cited herein comprise the state of the art and are incorporated herein by reference as though fully set forth.

What is claimed is:

1. A compound which is crystalline 8-chloro-3-pentyl-3,7-dihydro-1H-purine-2,6-dione tris(hydroxymethyl)aminomethane anhydrate:

Formula (A)

having an XRPD pattern as shown in FIG. 2.

2. A compound which is crystalline 8-chloro-3-pentyl-3,7-dihydro-1H-purine-2,6-dione tris(hydroxymethyl)aminomethane anhydrate having an XRPD pattern comprising the following peaks:

| Position (±0.2° 2-theta) | d-spacing ((Å)) |
| --- | --- |
| 10.1 | 8.7 |
| 10.5 | 8.4 |
| 12.2 | 7.3 |
| 13.0 | 6.8 |
| 13.5 | 6.5 |
| 17.3 | 5.1 |
| 17.5 | 5.1 |
| 17.9 | 5.0 |
| 18.3 | 4.8 |
| 19.2 | 4.6 |
| 19.8 | 4.5 |
| 20.2 | 4.4 |
| 20.6 | 4.3 |
| 20.9 | 4.2 |
| 21.7 | 4.1 |
| 22.1 | 4.0 |
| 23.3 | 3.8 |
| 23.9 | 3.7 |
| 24.6 | 3.6 |
| 26.3 | 3.4 |
| 27.1 | 3.3 |
| 27.9 | 3.2 |
| 28.2 | 3.2 |
| 28.6 | 3.1 |
| 29.6 | 3.0 |

3. A compound which is crystalline 8-chloro-3-pentyl-3,7-dihydro-1H-purine-2,6-dione tris(hydroxymethyl)aminomethane anhydrate having a melting endotherm with an onset melting temperature of 212±2° C. in a DSC thermogram.

4. A compound which is crystalline 8-chloro-3-pentyl-3,7-dihydro-1H-purine-2,6-dione tris(hydroxymethyl)aminomethane anhydrate having an ATR IR spectrum with characteristic absorption peaks from: 3370, 3041, 2946, 2858, 1680, 1656, 1528, 1266, 1243, 1078, 1068 and 1049±1 cm-1.

5. A compound which is crystalline 8-chloro-3-pentyl-3,7-dihydro- 1H-purine-2,6-dione tris(hydroxymethyl)aminomethane anhydrate having an ATR IR spectrum as shown in FIG. 6.

6. A pharmaceutical formulation comprising:
 a) the compound as defined in claim 1; and
 b) one or more pharmaceutically acceptable carriers.

7. A method for preparing the compound as defined in claim 1, said method comprising a step of mixing a compound of Formula (A):

with tris(hydroxymethyl)aminomethane.

8. A method for preparing a pharmaceutical formulation comprising 8-chloro-3-pentyl-3,7-dihydro-1H-purine-2,6-dione tris(hydroxymethyl)aminomethane:

said method comprising:
 a) admixing the compound as defined in claim 1 with at least one of a liquid and a finely divided solid carrier, and
 b) optionally shaping the admixture.

9. A compound which is crystalline 8-chloro-3-pentyl-3,7-dihydro-1H-purine-2,6-dione tris(hydroxymethyl)aminomethane anhydrate having an XRPD pattern comprising peaks at 10.1, 10.5, 12.2, 13.0, 13.5, and 17.3 (±0.2° 2-theta).

10. A method for preparing a pharmaceutical formulation comprising 8-chloro-3-pentyl-3,7-dihydro-1H-purine-2,6-dione tris(hydroxymethyl)aminomethane:

said method comprising:
- a) admixing the compound as defined in claim 9 with at least one of a liquid and a finely divided solid carrier, and
- b) optionally shaping the admixture.

11. A pharmaceutical formulation comprising:
a) the compound as defined in claim 9; and
b) one or more pharmaceutically acceptable carriers.

* * * * *